(12) United States Patent
Weston et al.

(10) Patent No.: US 11,844,876 B2
(45) Date of Patent: Dec. 19, 2023

(54) TWO-PART CLOTTING COMPOSITION AND METHODS OF MAKING AND USING THEREOF

(71) Applicant: BioStem Technologies, Inc., Pompano Beach, FL (US)

(72) Inventors: Wendy W. Weston, Coral Springs, FL (US); Michelle R. House, West Palm Beach, FL (US); Jason Matuszewski, Boca Raton, FL (US)

(73) Assignee: BioStem Tehcnologies, Inc., Pompano Beach, FL (US)

( * ) Notice: Subject to any disclaimer, the term of this patent is extended or adjusted under 35 U.S.C. 154(b) by 0 days.

(21) Appl. No.: 17/794,718

(22) PCT Filed: Jan. 24, 2022

(86) PCT No.: PCT/US2022/013452
§ 371 (c)(1),
(2) Date: Jul. 22, 2022

(87) PCT Pub. No.: WO2022/159789
PCT Pub. Date: Jul. 28, 2022

(65) Prior Publication Data
US 2023/0241289 A1      Aug. 3, 2023

Related U.S. Application Data

(60) Provisional application No. 63/141,119, filed on Jan. 25, 2021.

(51) Int. Cl.
*A61L 27/36* (2006.01)
*A61K 35/51* (2015.01)
*A61K 38/17* (2006.01)
*A61K 38/39* (2006.01)

(52) U.S. Cl.
CPC .......... *A61L 27/3604* (2013.01); *A61K 35/51* (2013.01); *A61K 38/1754* (2013.01); *A61K 38/39* (2013.01); *A61L 2430/12* (2013.01)

(58) Field of Classification Search
None
See application file for complete search history.

(56) References Cited

U.S. PATENT DOCUMENTS

| | | |
|---|---|---|
| 8,685,732 B2 | 4/2014 | Font Perez et al. |
| 10,426,731 B2 | 10/2019 | Tseng et al. |
| 2010/0158880 A1 | 6/2010 | Seyda et al. |
| 2015/0335686 A1 | 11/2015 | Spencer et al. |

FOREIGN PATENT DOCUMENTS

WO    2019038411 A1    2/2019

OTHER PUBLICATIONS

International Search Report (ISR) for PCT/US2022/013452 dated Apr. 5, 2022 (4 pages).
Written Opinion (WO) for PCT/US2022/013452 dated Apr. 5, 2022 (7 pages).

*Primary Examiner* — Allison M Fox
(74) *Attorney, Agent, or Firm* — Shumaker, Loop & Kendrick, LLP

(57) ABSTRACT

A non-immunogenic two-part clotting composition derived from human umbilical cords and methods of making thereof. The non-immunogenic two-part clotting composition may be used for dental purposes (periodontic and/or endodontic purposes) such as packing a subject's gum post-tooth extraction and/or for other wound packing purposes.

24 Claims, 7 Drawing Sheets

TWO-PART CLOTTING COMPOSITION AND METHODS OF MAKING AND USING THEREOF

TECHNICAL FIELD

The present invention relates generally to the field of umbilical cord derived compositions, and more particularly, to a non-immunogenic, two-part clotting composition derived from human umbilical cords used for dental purposes and for wound packing in the medical field.

BACKGROUND

Compositions derived from human umbilical cords have various different uses in the medical field. For example, these advantageous uses may include harvesting stem cells therefrom for the potential treatment of various blood diseases, cancers, and immune system disorders. When preparing compositions derived from human umbilical cords, the umbilical cord tissue is often subjected to harsh mechanical and enzymatic processing conditions in which specific cells (e.g., stem cells) may isolated from the umbilical cord tissue, expanded/cultured, and cryopreserved, thus drastically altering the initial, endogenous cellular and extracellular profile of the umbilical cord tissue. Furthermore and either before, during, and/or after processing these umbilical cord isolates, exogenous additives, including various growth factors/cytokines such as interferon alpha (INF-α), are included within these isolates, which further alter these isolates when compared to the initial umbilical cord tissue. These alterations may further decrease efficacy in a desired treatment due to loss of the original, endogenous cellular and/or extracellular profile of the initial umbilical cord tissue.

SUMMARY

In view of the above, it is an object of the invention to provide compositions derived from human umbilical cord(s) that mimic, include, and/or retain a cellular and/or extracellular profile similar to the endogenous profile of a human umbilical cord (e.g., in vivo), especially when compared with various previously mentioned umbilical cord isolates. These compositions are prepared with fresh human umbilical cord (harvested and processed within 48 to 72 hours of extraction from the human subject) and, unlike the prior art compositions, are advantageously not subjected to biochemical and/or enzymatic digestion, which results in the compositions including and/or retaining a significant proportion of the cellular and/or extracellular profile (of a human umbilical cord in vivo).

In certain aspects, disclosed is a two-part clotting composition configured for wound packing and/or dental purposes and/or dental treatments including (a) a micronized human umbilical cord composition; and (b) an aqueous human umbilical cord filtrate configured to reconstitute the micronized human umbilical cord composition. In certain aspects, the aqueous human umbilical cord filtrate is a solution in which no settling, separation, and/or precipitation is observed after one month, two months, three months, four months, five months, six months, or more while being stored. In certain aspects and when preparing the two-part clotting composition, no exogenous enzymes are introduced therein, which avoids exogenous enzymatic degradation/digestion.

In certain aspects, the micronized human umbilical cord is a dried and/or milled micronized human umbilical cord tissue and is preferably not subjected to exogenous enzymatic digestion while preparing the dried and/or milled micronized human umbilical cord tissue.

In certain aspects, the micronized human umbilical cord composition has a particle diameter size ranging from greater than 1 µm to less than 300 µm. In certain aspects, the micronized human umbilical cord composition has a particle diameter size ranging from greater than 1 µm to 200 µm. In certain aspects, the micronized human umbilical cord composition has a particle diameter size ranging from greater than 1 µm to 100 µm. In certain aspects, the micronized human umbilical cord composition has a particle diameter size ranging from greater than 1 µm to 50 µm. In certain aspects, the micronized human umbilical cord composition has a particle diameter size ranging from greater than 1 µm to 25 µm. Moreover, the particles of the micronized human umbilical cord are polydisperse.

In certain aspects, the micronized human umbilical cord composition comprises collagen, fibronectin, insulin growth factor binding protein-1 (IGFBP-1), sulfated glycosaminoglycans (sGAGs), hyaluronan, or any combination thereof.

In certain aspects, the micronized human umbilical cord composition is dried micronized human umbilical cord tissue having a particle diameter size ranging from greater than 1 µm to 200 µm and comprising IGFBP-1, sGAGs, collagen, fibronectin, hyaluronan, or any combination thereof.

In certain aspects, the aqueous human umbilical cord filtrate comprises acellular Wharton's jelly, exosomes, endogenous growth factors, vascular endothelial growth factor receptor 1 (VEGFR1), hepatocyte growth factor (HGF), interleukin antagonists (interleukin-1 receptor antagonist (IL-1ra)), basic fibroblast growth factor (bFGF or FGF-2), platelet derived growth factor-BB (PDGF-BB), hyaluronan or a combination thereof.

In certain aspects, the aqueous human umbilical cord filtrate further includes an isotonic solution.

In certain aspects, the isotonic solution is phosphate buffered saline (1× PBS), lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasmalyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4).

In certain aspects, the aqueous human umbilical cord filtrate comprises particles from a human umbilical cord tissue therein that are less than 100 µm in diameter therein and that are preferably less than 50 µm in diameter, more preferably less than 25 µm in diameter, even more preferably less than 10 µm in diameter.

In certain aspects, the micronized human umbilical cord composition and the aqueous human umbilical cord filtrate are configured for admixing at a ratio of 2:1 to 1:2, wherein when mixed within this ratio, the admixed composition forms a paste.

In certain aspects, both the micronized human umbilical cord composition and the aqueous human umbilical cord filtrate are sterile.

In certain aspects, both the micronized human umbilical cord composition and the aqueous human umbilical cord filtrate are non-immunogenic.

In certain aspects, the two-part clotting composition is configured for wound packing. In this aspect (and when the two parts are admixed), the composition is preferably a paste having a sufficient thickness and consistency to induce blood clotting.

In certain aspects, wound packing comprises packing a cavity in a subject's gum(s) with the two-part clotting composition post-tooth extraction to induce blood clotting and promote wound healing therein.

In certain aspects, the two-part clotting composition has the consistency of a paste. In alternative aspects, ratios of the individual components can be varied when mixing each component together to form a lotion (i.e., a composition having a reduced viscosity when compared to the above-mentioned paste).

Also disclosed are kits comprising the two-part clotting composition configured for wound packing, the two-part clotting composition including: (a) a micronized human umbilical cord composition preloaded into a sterile syringe; and (b) an aqueous human umbilical cord filtrate preloaded into a sterile container that is separate from the micronized human umbilical cord composition, an aqueous human umbilical cord filtrate is configured to reconstitute the micronized human umbilical cord composition. In certain aspects, the kit further includes a second sterile syringe for mixing the disclosed compositions. In certain aspects and when preparing the two-part clotting composition, no exogenous enzymes are introduced therein, which avoids exogenous enzymatic degradation/digestion.

In certain aspects, the micronized human umbilical cord of the kit is a dried or milled micronized human umbilical cord tissue and is preferably not subjected to exogenous enzymatic digestion.

In certain aspects, the micronized human umbilical cord of the kit composition has a particle diameter size ranging from greater than 1 μm to less than 300 μm. Moreover, the particles of the micronized human umbilical cord are polydisperse.

In certain aspects, the micronized human umbilical cord composition of the kit has a particle diameter size ranging from greater than 1 μm to 200 μm.

In certain aspects, the micronized human umbilical cord composition of the kit has a particle diameter size ranging from greater than 1 μm to 100 μm. In certain aspects, the micronized human umbilical cord composition of the kit has a particle diameter size ranging from greater than 1 μm to 50 μm. In certain aspects, the micronized human umbilical cord composition of the kit has a particle diameter size ranging from greater than 1 μm to 25 μm.

In certain aspects, the micronized human umbilical cord composition of the kit comprises collagen, fibronectin, IGFBP-1, sGAGs, hyaluronan, or any combination thereof.

In certain aspects, the micronized human umbilical cord composition of the kit is dried micronized human umbilical cord tissue having a particle diameter size ranging from greater than 1 μm to less than 300 μm and comprising collagen, fibronectin, IGFBP-1, sGAGs, hyaluronan, or any combination thereof.

In certain aspects, the aqueous human umbilical cord filtrate of the kit comprises acellular Wharton's jelly, exosomes, endogenous growth factors, VEGFR1, HGF, interleukin antagonists (IL-1ra), bFGF, PDGF-BB, hyaluronan or a combination thereof.

In certain aspects, the aqueous human umbilical cord filtrate of the kit further comprises an isotonic solution.

In certain aspects, the isotonic solution of the kit is phosphate buffered saline (1× PBS), lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasmalyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4).

In certain aspects, the aqueous human umbilical cord filtrate of the kit comprises particles from a human umbilical cord tissue that are less than 100 μm in diameter therein and that are preferably less than 50 μm in diameter, more preferably less than 25 μm in diameter, even more preferably less than 10 μm in diameter. In certain aspects, the aqueous human umbilical cord filtrate is a solution in which no settling, separation, and/or precipitation is observed after one month, two months, three months, four months, five months, six months, or more while being stored.

In certain aspects, the micronized human umbilical cord composition and the aqueous human umbilical cord filtrate of the kit are configured for admixing at a ratio of 2:1 to 1:2.

In certain aspects, both the micronized human umbilical cord composition and the aqueous human umbilical cord filtrate of the kit are sterile.

In certain aspects, both the micronized human umbilical cord composition and the aqueous human umbilical cord filtrate of the kit are non-immunogenic.

In certain aspects, the two-part clotting composition of the kit is configured for wound packing. In certain aspects, the wound packing comprises packing a cavity in a subject's gum(s) with the two-part clotting composition post-tooth extraction to induce blood clotting and promote wound healing therein.

In certain aspects, also disclosed is a method of packing a subject's gums post-tooth extraction including (a) mixing (sterilely mixing) the composition at an effective viscosity to induce blood clotting; and (b) packing (sterilely packing) a cavity within the subject's gums formed by tooth extraction with the mixed composition of step (a) to induce blood clotting within the packed cavity. In certain aspects, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate.

In certain aspects, also disclosed is a method of packing a subject's wound comprising: (a) sterilely mixing the composition disclosed herein at an effective viscosity to induce blood clotting; and (b) sterilely packing the subject's wound with the sterilely mixed composition of step (a) to induce blood clotting within the sterilely packed wound. In this aspect, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate.

In certain aspects, also disclosed are methods of treating an orthopedic and/or podiatric conditions/ailments. For example, in certain aspects, plantar fasciitis and/or heel ailments may be treated by injecting the mixed two part composition disclosed herein directly into the subject's foot (subcutaneously in a portion between the ball and heel of the foot) and/or immediately adjacent to the portion of bone forming the subject's heel. This method comprises: (a) sterilely mixing the composition disclosed herein at an effective viscosity to treat a subject having orthopedic and/or podiatric conditions/ailments (e.g., plantar fasciitis); and (b) sterilely injecting the sterilely mixed composition of step (a) into and/or adjacent the area of the subject affected with orthopedic and/or podiatric conditions/ailments thereby treating the condition/ailment. In this aspect, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate to have sufficient viscosity to treat the condition/ailment. For example, when treating ones plantar fasciitis with the above method and compositions, the mixed compositions have sufficient thickness and viscosity to provide cushioning (subcutaneous cushioning) to treat and mitigate pain associated with plantar fasciitis. In particular, the high viscosity of the filtrate provides the desired cushioning effect, and the Wharton's Jelly (mucopolysaccharides and proteoglycans) in the filtrate further aid in the cushioning and protective purposes of the above mentioned treatment(s).

In certain aspects, each individual component of the two-part clotting compositions disclosed herein may be used individually (alone) for specified purposes. For example, when using the disclosed filtrate individually, the purpose of using all filtrate would be to provide the cushioning and/or lubrication activity, growth factors and exosomes within the filtrate without introducing a scaffolding or stromal substrate. For example, if one were to use the filtrate to provide cushioning substance to a degenerative heel pad or mix with commercially available bone particulate for application to a tooth socket. As another example and when using the disclosed micronized compositions individually (alone), the purpose of using all particulate would be to pack a wet wound bed or dental socket when the area is too wet to add additional filtrate, or another filtrate is desired, such as platelet rich plasma (PRP).

In additional aspects, also disclosed is a method of making a two-part clotting composition configured for wound packing and/or dental purposes and/or dental treatments, the method comprising: (a) providing a human umbilical cord; (b) washing the human umbilical cord with an isotonic solution; (c) grinding the washed human umbilical cord of step (b) thereby forming ground human umbilical cord tissue; (d) separating the ground human umbilical cord tissue of step (c) into a solid retentate and an aqueous human umbilical cord supernatant; (e) further processing the solid retentate of step (d) into a micronized human umbilical cord composition; and (f) filtering and diluting the aqueous human umbilical cord supernatant thereby forming an aqueous human umbilical cord filtrate configured to reconstitute the micronized human umbilical cord composition when admixed with one another, the aqueous human umbilical cord filtrate having particles from the ground human umbilical cord tissue that are less than 100 μm in diameter therein. In this aspect, none of steps (a)-(f) include introduction of exogenous enzymes resulting in exogenous enzymatic degradation/digestion.

In certain aspects the human umbilical cord of the method is obtained from a subject and is subsequently subjected to steps (a)-(c) within 48 to 96 hours, more preferably within 48 to 72 hours post-childbirth and/or caesarean section and/or human umbilical cord extraction event.

In certain aspects, the method further comprises, between steps (a)-(c), removing any blood clots present within the human umbilical cord.

In certain aspects, step (b) is repeated between one to five times by discarding the used isotonic solution, and providing new isotonic solution and again washing the human umbilical cord with the new isotonic solution.

In certain aspects, 15 to 80 grams of human umbilical cord is provided in step (a) and is subsequently subjected to steps (b)-(f).

In certain aspects, the isotonic solution is phosphate buffered saline (or one of lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasmalyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4)) provided at a volume ranging from 300 mL to 1000 mL per washing step (b).

In certain aspects, a grinding tool configured to grind and/or mince the washed human umbilical cord is used during step (c) and grinds the washed human umbilical cord at a range of 40 to 200 revolutions per minute (RPM) until the umbilical cord has been fully ground.

In certain aspects, the method includes before step (d) contacting the ground umbilical cord tissue formed in step (c) with a filter and subsequently filtering the ground umbilical cord tissue to form the solid retentate retained on the filter and the aqueous human umbilical cord supernatant of step (d) that has passed through the filter. In this aspect, the filter has a porosity ranging from 100 μm to 200 μm.

In certain aspects, the further processing step of step (e) is a milling, freeze drying, or dehydration process that forms the micronized human umbilical cord composition of step (e) having particle sizes ranging from greater than 1 μm to less than 300 μm and more preferably particle sizes ranging from greater than 1 μm to 100 μm and even more preferably from greater than 1 μm to 50 μm and even more preferably from greater than 1 μm to 25 μm. Moreover, the particles of the micronized human umbilical cord are polydisperse.

In certain aspects, the further processing step of step (e) is a cryomilling process in which the solid retentate of step (d) is placed into a liquid nitrogen cooled cryomill chamber and subjected to grinding therein thereby forming the micronized human umbilical cord composition having particle sizes ranging from greater than 1 μm to less than 300 μm and more preferably particle sizes ranging from greater than 1 μm to 100 μm, and even more preferably from greater than 1 μm to 50 μm and even more preferably from greater than 1 μm to 25 μm. Moreover, the particles of the micronized human umbilical cord are polydisperse.

In certain aspects, step (f) comprises a plurality of filtration steps comprising: (i) filtering the aqueous human umbilical cord supernatant through a first filter having a porosity ranging from 30 μm to 40 μm thereby forming a second human umbilical cord supernatant; (ii) filtering the second human umbilical cord supernatant through a second filter having a porosity ranging from 12.5 μm to 25 μm thereby forming a third human umbilical cord supernatant; and (iii) filtering the third human umbilical cord supernatant through a third filter having a porosity ranging from 4 μm to 10 μm thereby forming the aqueous human umbilical cord filtrate. Thus, in certain aspects, the second human umbilical cord supernatant would include particles from the human umbilical cord tissue that are less than 40 um; the third human umbilical cord supernatant would include particles from the human umbilical cord tissue that are less than 25 um; and the aqueous human umbilical cord filtrate would include particles from the human umbilical cord tissue that are less than 10 um. In certain aspects, the aqueous human umbilical cord filtrate is a solution in which no settling, separation, and/or precipitation is observed after one month, two months, three months, four months, five months, six months, or more while being stored.

In certain aspects, the micronized human umbilical cord composition of the method comprises collagen, fibronectin, IGFBP-1, sGAGs, hyaluronan, or any combination thereof.

In certain aspects, the micronized human umbilical cord of the method composition is a dried micronized human umbilical cord tissue having a particle diameter size ranging from greater than 1 μm to 300 μm and comprising collagen, fibronectin, IGFBP-1, sGAGs, hyaluronan, or any combination thereof.

In certain aspects, the aqueous human umbilical cord filtrate of the method comprises acellular Wharton's jelly, exosomes, endogenous growth factors, VEGFR1, HGF, interleukin antagonists (IL-1ra), bFGF, PDGF-BB, hyaluronan or a combination thereof.

In certain aspects, both the micronized human umbilical cord composition and the aqueous human umbilical cord filtrate of the method are sterile.

In certain aspects, both the micronized human umbilical cord composition and the aqueous human umbilical cord filtrate of the method are non-immunogenic.

In certain aspects, the method further comprises (g) placing and sealing the micronized human umbilical cord composition in a first sterile container for subsequent use and placing and sealing the aqueous human umbilical cord filtrate in a second sterile container for subsequent use, wherein both the micronized human umbilical cord composition and the aqueous human umbilical cord filtrate are sterile and are configured to form a paste or lotion when admixed with one another.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

Figure 1:
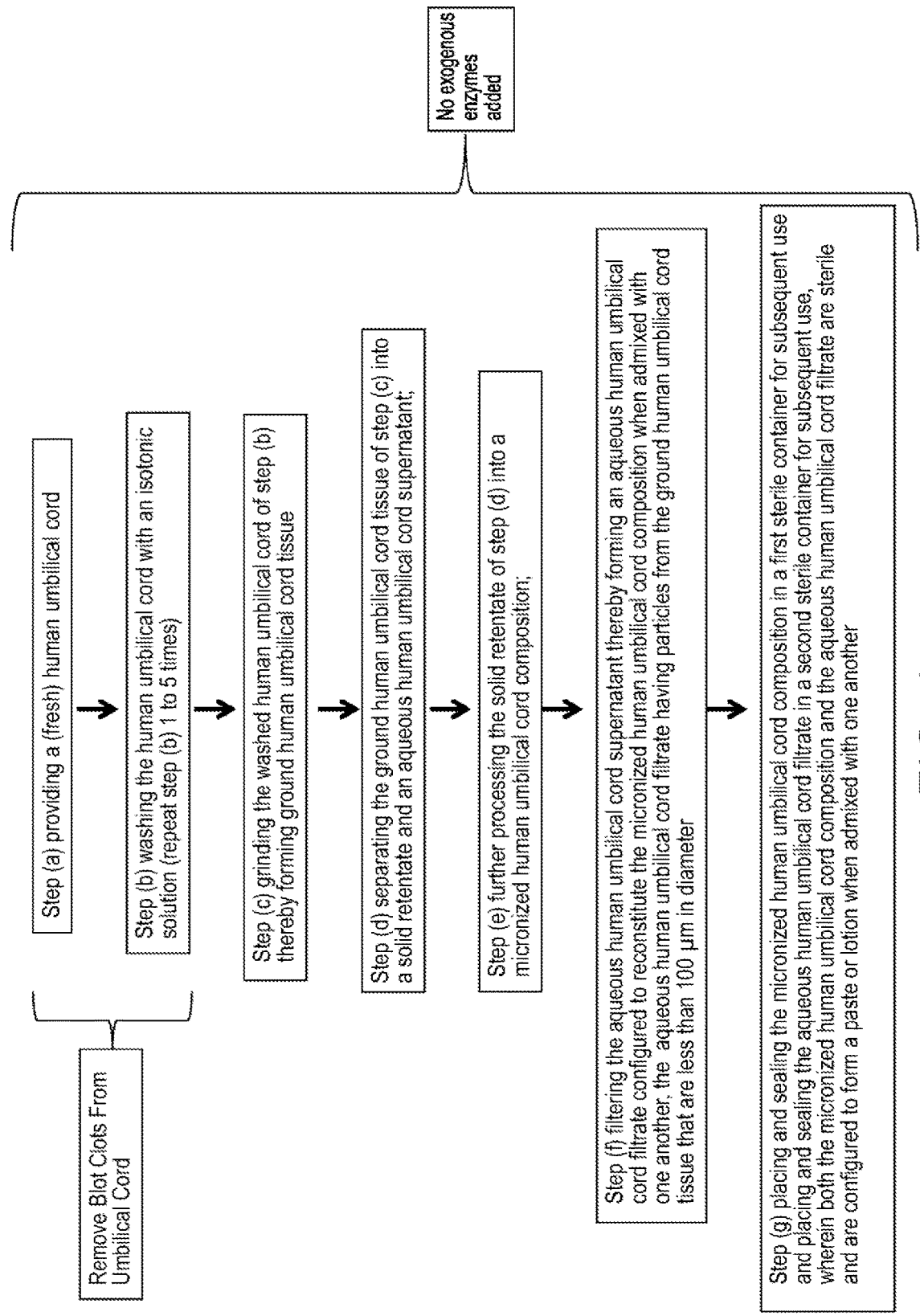
FIG. 1 is a schematic depiction of the steps included for making the two parts of the two-part clotting composition.

The present invention will now be described mom fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings. Moreover, in this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

The compositions and methods described herein can comprise, consist of, or consist essentially of the essential elements and limitations described herein, as well as any additional or optional ingredients, components, or limitations described herein.

Two-Part (Clotting) Composition

Disclosed herein are two-part compositions derived from human umbilical cord(s), and when each component is mixed with one another, the resulting composition mimics, includes, and/or retains a cellular and/or extracellular profile similar to the endogenous profile of a human umbilical cord, for example, in vivo, especially when compared with various previously mentioned umbilical cord isolates. These compositions are prepared with fresh human umbilical cord (harvested and processed within 48 to 72 hours of extraction from the human subject) and, unlike compositions in the prior art, are advantageously not subjected to biochemical and/or enzymatic digestion, which results in the compositions including and/or retaining a significant portion of the cellular and/or extracellular profile (when compared to the endogenous profile of a human umbilical cord in vivo). Moreover because of the ease and convenience of preparing (sterile preparation) these compositions (e.g., point of use preparation and use within a dental office, medical office, or emergency room) and because of the non-immunogenic characteristics of these compositions, these compositions may be used as allografts within humans for numerous different medical purposes and medical procedures, which, include but are not limited to, dental procedures (such as gum packing—post-tooth extraction) and/or general wound packing.

Disclosed herein are two-part compositions (e.g., clotting compositions) that include (a) a micronized human umbilical cord composition; and (b) an aqueous human umbilical cord filtrate configured to reconstitute the micronized human umbilical cord composition, which may be configured for wound packing and/or dental purposes and/or dental treatments. In certain aspects and when preparing the two-part composition (e.g., clotting composition), no exogenous enzymes are introduced therein, which avoids exogenous enzymatic degradation/digestion and further ensures that these compositions have an improved endogenous cellular and extracellular profile (similar to human umbilical cord in vivo) especially when compared to conventional compositions utilizing umbilical cord tissues and/or cells derived therefrom.

In certain aspects, the micronized human umbilical cord is a dried and/or milled (e.g., cryomilled) micronized human umbilical cord tissue. As alluded to above, the micronized human umbilical cord preferably not subjected to exogenous enzymatic digestion while preparing the dried and/or milled micronized human umbilical cord tissue, which further preserves and/or reduces degradation of endogenous collagens, fibronectin, hyaluronan, or any combination thereof therein. These collagens fibronectin, hyaluronan, or any combination thereof therein may advantageously play a role in improving clotting time within a subject while collagens fibronectin and hyaluronan, concurrently and advantageously promote wound healing therein.

Figure 5:
FIG. 5 shows exemplary sieves used in the process of generating polydisperse particulates having the sizes disclosed herein.
Figure 5:
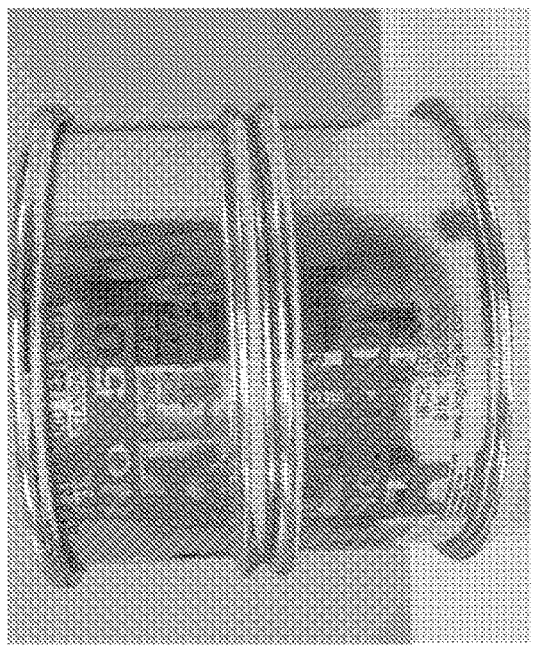
Figure 6:
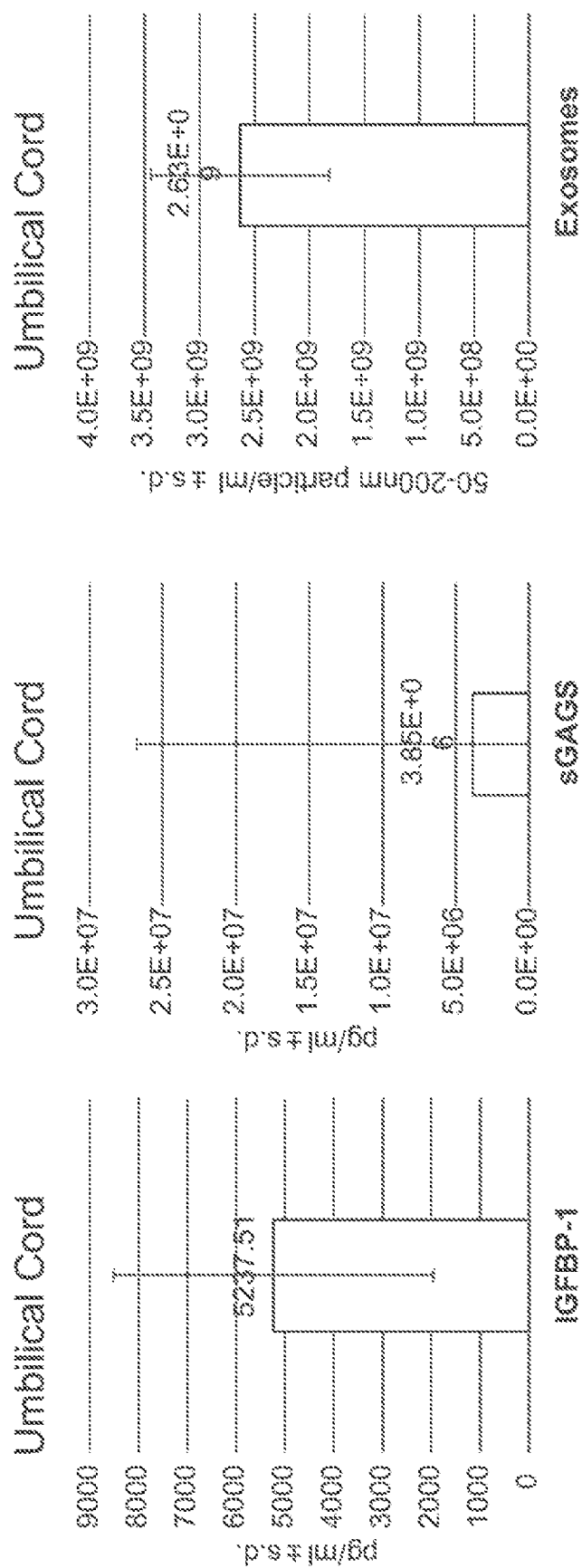
FIG. 6 are graphs showing the concentration profiles of IGFBP-1, sGAGs, and exosomes in the micronized human umbilical cord composition.

Moreover, the micronized human umbilical cord composition has a particle diameter size ranging from greater than 1 μm to less than 300 μm, from greater than 1 μm to 100 μm, greater than 1 μm to 50 μm, or greater than 1 μm to 25 μm so that adequate mixing, wetting, and/or reconstitution of the micronized human umbilical cord composition occurs when mixed with the aqueous human umbilical cord filtrate. Moreover, the particles within the micronized human umbilical cord composition are polydisperse. It is further envisioned that any endpoint falling within the above disclosed ranges may serve as additional ranges. In certain aspects and when micronized human umbilical cord composition particle diameters exceed 300 μm, poor mixing, wetting, and/or reconstitution is observed, which ultimately leads to either an inoperable and/or suboptimal paste/allograft composition disclosed herein. FIG. 5 depicts exemplary sieves used in the process of generating polydisperse particulates/particles having the sizes disclosed herein. Moreover FIG. 6 depicts graphs showing the concentration profiles of IGFBP-1, sGAGs, and exosomes in the micronized human umbilical cord composition in which IGFBP-1 ranges from ~1500 pg/mL to ~9000 pg/mL, sGAGs ranges from $0.1\times10^6$ pg/ml to $3.0\times10^7$ pg/ml, and exosomes from $1.5\times10^9$ particles/ml to $4.0\times10^9$ particles/mi (in which the exosome particle size ranges from 50 to 200 nm) in the micronized human umbilical cord composition. In certain aspects, any endpoint falling within the above-mentioned ranges can serve as endpoints for any additional ranges falling in between. In certain aspects, the sGAGs may optionally be excluded from the micronized human umbilical cord composition.

Figure 7:
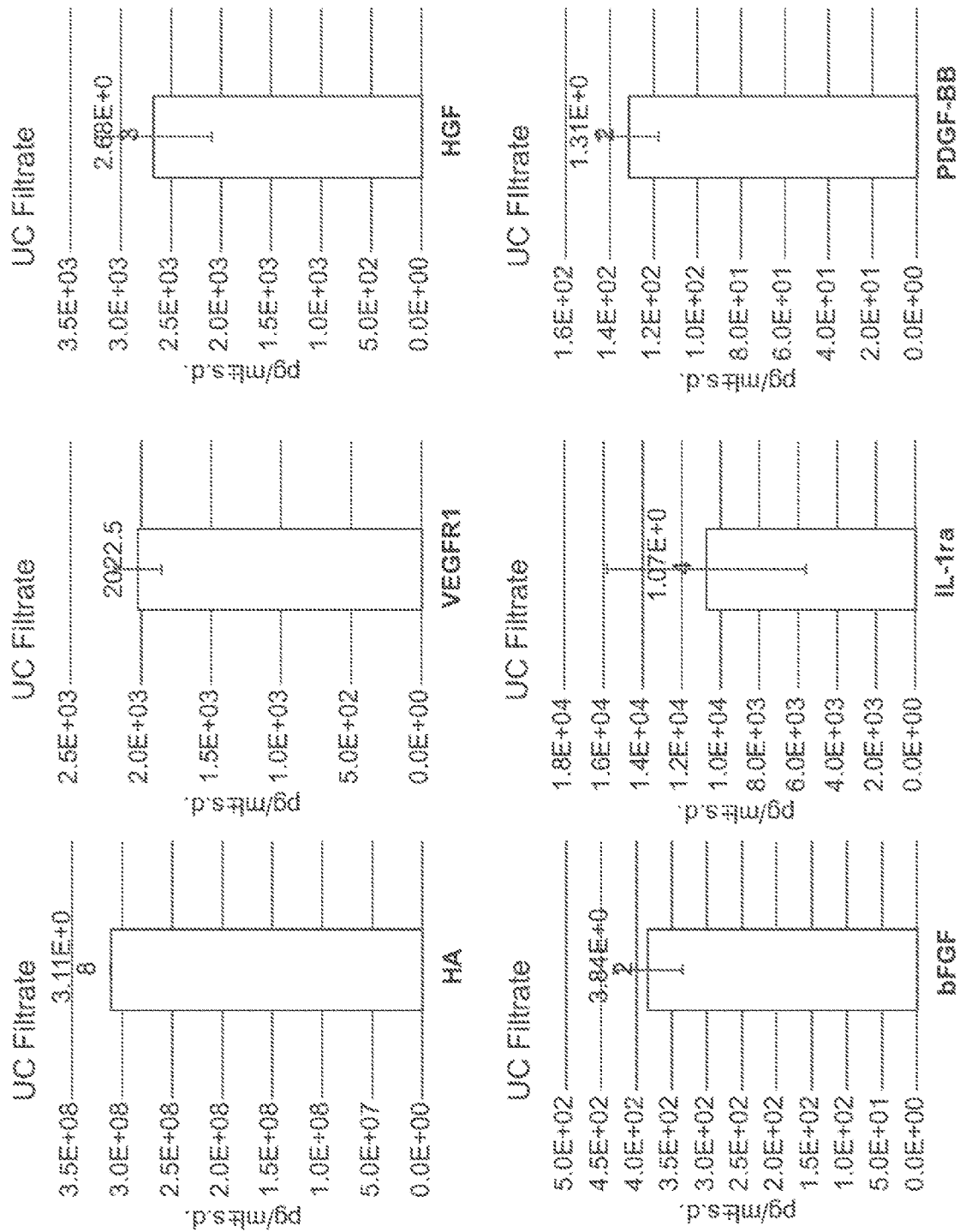
FIG. 7 are graphs showing the concentration profiles of VEGFR1. HGF, interleukin antagonists (IL-1ra), bFGF, PDGF-BB and hyaluronan in the aqueous human umbilical cord filtrate.

As alluded to above, the second component of the two-part compositions include an aqueous human umbilical cord filtrate that is configured to reconstitute the micronized human umbilical cord composition. The aqueous human umbilical cord filtrate is prepared, preferably from the same umbilical cord as the micronized human umbilical cord (disclosed above) via one or more separation steps (e.g., filtration steps) when preparing the micronized human umbilical cord. The human umbilical cord filtrate preferably includes acellular Wharton's jelly, exosomes, endogenous growth factors, vascular endothelial growth factor receptor 1 (VEGFR1), hepatocyte growth factor (HGF), interleukin antagonists (IL-1ra), bFGF, PDGF-BB, hyaluronan (HA) or a combination thereof therein, which advantageously promotes wound healing within a subject when the disclosed compositions are used for their desired purpose. As shown in FIG. 7, within the filtrate the concentrations of HA ranges from $3.0\times10^8$ pg/ml to $3.2\times10^8$ pg/ml ($2.0\times10^7$ pg/ml to $2.1\times10^7$ pg/ml after dilution with isotonic solution), VEGFR 1 ranges from $1.8\times10^3$ pg/mi to $2.2\times10^3$ pg/ml ($1.2\times10^2$ pg/nil to $1.5\times10^2$ pg/ml after dilution with isotonic solution), HGF ranges from $2.1\times10^3$ pg/ml to $3.3\times10^3$ pg/ml ($1.4\times10^2$ pg/ml to $2.2\times10^2$ pg/ml after dilution with isotonic solution), bFGF ranges from $3.3\times10^2$ pg/ml to $4.3\times10^2$ pg/ml (22 pg/ml to 29 pg/ml after dilution with isotonic solution), IL-1ra ranges from $5.6\times10^3$ pg/ml to $1.6\times10^4$ pg/ml ($3.7\times10^2$ pg/ml to $1.1\times10^3$ pg/ml after dilution with isotonic solution), and PDGF-BB ranges from 117 pg/ml to 145 pg/ml (7.8 pg/ml to 9.7 pg/ml after dilution with isotonic solution). In certain aspects, any endpoint falling within the above-mentioned ranges can serve as endpoints for any additional ranges falling in between. In certain aspects, the aqueous human umbilical cord filtrate may include particles that remain from a human umbilical cord tissue therein that are less than 100 μm in diameter, preferably less than 50 μm in diameter, more preferably less than 25 μm in diameter, even more preferably less than 10 μm in diameter. Moreover, aqueous human umbilical cord filtrate is a solution in which no settling, separation, and/or precipitation is observed after one month, two months, three months, four months, five months, six months, or more while being stored. In certain aspects and due to the preparation steps of these compositions as disclosed immediately below as well as in FIG. 1, the aqueous human umbilical cord filtrate further includes an isotonic solution such as phosphate buffered saline (or one of lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasmalyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4)), which merely aids in the preparation of each component of the two-part compositions disclosed herein and further has no and/or minimal degradative effects on, for example, acellular Wharton's jelly, exosomes, endogenous growth factors, VEGFR1, HGF, interleukin antagonists (e.g. IL-1ra), bFGF, PDGF-BB, hyaluronan or a combination thereof within the aqueous human umbilical cord filtrate. In certain aspects, it is envisioned that amniotic fluid may be used either in addition to or in lieu of the aqueous human umbilical cord filtrate disclosed herein. Amniotic fluid has a high concentration of human growth factor (HGF), which may be desired when using the disclosed composition. Although amniotic fluid has a lower viscosity than the umbilical cord filtrate, amniotic fluid contains monocyte chemoattractant proteins (MCP), EGF and other endogenous growth factors in common with the umbilical cord filtrate, and thus may be a viable substitute for filtrate disclosed herein for certain uses.

As further alluded to above, the compositions (when mixed) may be used as allografts within humans for numerous different purposes and procedures, which, include but are not limited to, dental procedures (such as gum packing— post-tooth extraction) and/or general wound packing. In this aspect, it is important to maintain sterility of the human umbilical cord composition and the aqueous human umbilical cord filtrate are both preferably sterile both before mixing with one another as well as post-mixing with one another. It should be noted that the micronized human umbilical cord composition and the aqueous human umbilical cord filtrate are non-immunogenic, and thus, should induce very little immune response within a subject when used for its desired purpose. However, sterility should be maintained such that contaminants (e.g., viral contaminants, bacterial contaminants, chemical contaminants, etc.) are not introduced into the composition that may induce an immune response and/or infect a wound when the composition is placed in a subject. Moreover, the micronized human umbilical cord composition and the aqueous human umbilical cord filtrate are configured for admixing to form pastes and lotions having varied viscosities/thicknesses, and the micronized human umbilical cord composition and the aqueous human umbilical cord filtrate may be mixed at a ratio of 2:1 to 1:2 when forming the pastes and/or lotions disclosed herein.

In certain aspects, the two-part clotting composition is configured for wound packing. In this aspect (and when the two parts are admixed with one another), the resulting composition is preferably a paste having a sufficient thickness and consistency to induce blood clotting. For example, this composition may be packed within a subject's gum(s) post-tooth extraction to induce blood clotting and promote wound healing therein. It is also, envisioned that this composition may be packed within other wounds for substantially similar purposes.

Method of Making Two-Part Clotting Composition

FIG. 1 provides a schematic depiction of the steps included for making the two parts (i.e., particulate part and supernatant/filtrate part) of the two-part clotting composition disclosed herein, and as further shown in FIG. 1, none of steps include introduction of exogenous enzymes resulting in exogenous enzymatic degradation/digestion. The method of making a two-part clotting composition configured for wound packing and/or dental purposes and/or dental treatments, the method including steps (a)-(g) discussed immediately below. Before step (a), the umbilical cord is screened for communicable diseases to ensure that the umbilical cord/umbilical cord tissue is healthy/disease free and to further minimize risk during preparation and subsequent end use of the two-part clotting compositions. After confirming that the umbilical cord/umbilical cord tissue is healthy/disease free, the umbilical cord is maintained at temperature ranging from 4° C. to 8° C. before beginning the processing of the cord in steps (a)-(g).

As shown in FIG. 1, step (a) includes providing a human umbilical cord preferably within 24 to 96 hours post-extraction from a human subject, more preferably from 24 to 72 hours post-extraction from a human subject to ensure freshness of the human umbilical cord (i.e., tissue and cells comprising the tissue) and to minimize degradation associated (enzymatic degradation) resulting from necroptosis and/or apoptosis. In this step and in order for appropriate grinding/mincing to occur (in subsequent step (c)), it is preferred that 15 to 80 gram portions and more preferably 30 to 60 gram portions of the human umbilical cord are subjected to the below mentioned method, with the average portions being approximately 40 grams.

After completing step (a), step (b) occurs. Step (b) includes placing one or more umbilical cord portions (15 to 80 gram) into a container having a predetermined volume (e.g., 300 mL to 1000 mL, preferably 500 mL) of isotonic solution in which the isotonic solution is preferably phosphate buffered saline (PBS) (i.e., 1× PBS)(or alternatively one of lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasmalyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4)). Placing the container onto a stir plate and placing a stir bar within the container (containing the PBS and umbilical cord portions) therein and stirring (medium to high speed) the umbilical cord portions within the isotonic solution for 5 to 15 minutes to wash the umbilical cord portions. Next, washing step (b) is repeated one to five times by decanting the "used" isotonic solution and pouring new isotonic solution into the container at a predetermined volume (e.g., 300 mL to 1000 mL, preferably 500 mL) to again wash the one or more umbilical cord portions. Either before step (a), during step (a), before step (b), or during step (b) further determining whether any blood clots and/or blood pool(s)/ pooling are present in the human umbilical cord and/or umbilical cord portions, and if so, removing these blood clots via suction or other mechanical removal means (e.g., scalpel and forceps) to further ensure that the presence of any immunogenic components (e.g., hemoglobin and/or heme associated components from the umbilical cord donor) are minimized in the end resulting two-part clotting composition. During these washing steps, it is imperative to maintain an aseptic and/or sterile work environment to prevent and/or reduce introduction of any contaminants while making the two-part clotting composition.

Upon concluding step (b), step (c) is performed in which the washed umbilical cord/umbilical cord portions (being within a predetermined volume (e.g., 75 mL to 125 mL, preferably 100 mL) of the isotonic solution) are transferred to a grinding and/or mincing apparatus such as those disclosed in U.S. D716,601 "Tissue Mincing Tool" and/or U.S. Pat. No. 8,967,512 "Systems And Methods For Processing Cells", which are incorporated by reference herein in their entirety. The washed umbilical cord/umbilical cord portions are subsequently subjected to grinding and/or mincing by the grinding/mincing tool with the head of the grinding/mincing tool rotating at a range of 40 to 200 revolutions per minute (RPM) until the umbilical cord has been fully ground thereby forming ground human umbilical cord tissue. During this grinding/mincing step, it is imperative to maintain a sterile work environment to prevent and/or reduce introduction of any contaminants while making the two-part clotting composition. In certain aspects, the grinding/mincing tool may be directly connected to an apparatus (i.e., a closed system environment as disclosed, for example, in U.S. Pat. No. 8,967,512) to further conduct steps (d)-(f) discussed below and to further maintain sterility and/or minimize the introduction of any contaminants while making the two-part clotting composition. Alternatively, steps (d)-(f) maybe conducted in an open system/laboratory environment while performing each of the below mentioned steps.

Upon concluding step (c), step (d) is performed in which the ground/minced human umbilical cord tissue of step (c)

is separated into a solid retentate and an aqueous human umbilical cord supernatant. This initial separation step may occur via a filtration process (either positive or negative pressure). For example, the minced/ground human umbilical cord tissue (of step (c) and included within a predetermined volume (e.g., 75 mL to 125 mL, preferably 100 mL) of the isotonic solution) may be placed directly on a filter having a desired porosity (e.g., 200 µm or 150 µm or 100 µm such as either a qualitative grade or quantitative grade mesh or net filter) and then force (either positive or negative pressure) may or may not be applied such that a solid retentate (solids having a size above 200 µm or 150 µm or 100 µm) remain on the filter while an aqueous human umbilical cord supernatant (having any solids therein that are less than (200 µm or 150 µm or 100 µm) are passed through the filter. The filtration step generally takes 15 seconds to 2 minutes. Again, it is imperative to maintain a sterile and/or aseptic work environment to prevent and/or reduce introduction of any contaminants throughout step (d).

Upon concluding step (d), step (e) is performed that the solid retentate of step (d) is further processed into a micronized human umbilical cord composition by subjecting the solid retentate to a milling, freeze drying (cryomilling), and/or dehydration (lyophilization) process configured to yield particles (polydisperse particles) having sizes ranging from greater than 1 µm to 300 µm, preferably greater than 1 µm to 100 µm, and more preferably greater than 1 µm to 50 µm and more preferably greater than to than 1 µm to 25 µm. In certain aspects, step (e) is a cryomilling process (as described, for example, US 20160287749, US 20170203004, and U.S. patent Ser. No. 10/105,398, which are each incorporated by reference in their entirety herein) in which the solid retentate of step (d) is placed into a liquid nitrogen cooled cryomill chamber and subjected to grinding therein thereby forming the micronized human umbilical cord composition having particle sizes ranging from greater than 1 µm to less than 300 µm, preferably greater than 1 µm to 100 µm, more preferably greater than 1 µm to 50 µm, and even more preferably from greater than 1 µm to 25 µm. The micronized human umbilical cord composition comprises collagen, fibronectin, hyaluronan, elastins, or any combination thereof.

Upon concluding step (d) and either concurrently with (and/or either before or during step (e)), step (f) is performed on the aqueous human umbilical cord supernatant. Step (f) preferably includes a plurality of filtration steps including: (i) filtering the aqueous human umbilical cord supernatant through a first filter having a porosity ranging from 30 µm to 40 µm thereby forming a second human umbilical cord supernatant; (ii) filtering the second human umbilical cord supernatant through a second filter having a porosity ranging from 12.5 µm to 25 µm thereby forming a third human umbilical cord supernatant; and (iii) filtering the third human umbilical cord supernatant through a third filter having a porosity ranging from 4 µm to 10 µm thereby forming the aqueous human umbilical cord filtrate. The filtration step generally takes 15 seconds to 2 minutes at 1-5 psi vacuum to complete. In certain aspects, the force applied is a negative pressure (vacuum) and preferred because such negative pressure is less likely to damage the filter and lead to subsequent quality control issues with the resulting two-part compositions disclosed herein. The aqueous human umbilical cord filtrate preferably includes acellular Wharton's jelly, exosomes, endogenous growth factors, VEGFR1, HGF, interleukin antagonists IL-1ra), bFGF, PDGF-BB, hyaluronan, or any combination thereof. Each filtration step generally takes 15 seconds to 2 minutes at 1-5 psi vacuum to complete. Moreover, the resulting aqueous human umbilical cord filtrate from the above mentioned filtration steps is a solution in which no settling, separation, and/or precipitation is observed after one month, two months, three months, four months, five months, six months, or more while being stored.

In certain aspects, both the micronized human umbilical cord composition and the aqueous human umbilical cord filtrate are sterile, and both the micronized human umbilical cord composition and the aqueous human umbilical cord filtrate are non-immunogenic.

Figure 2:
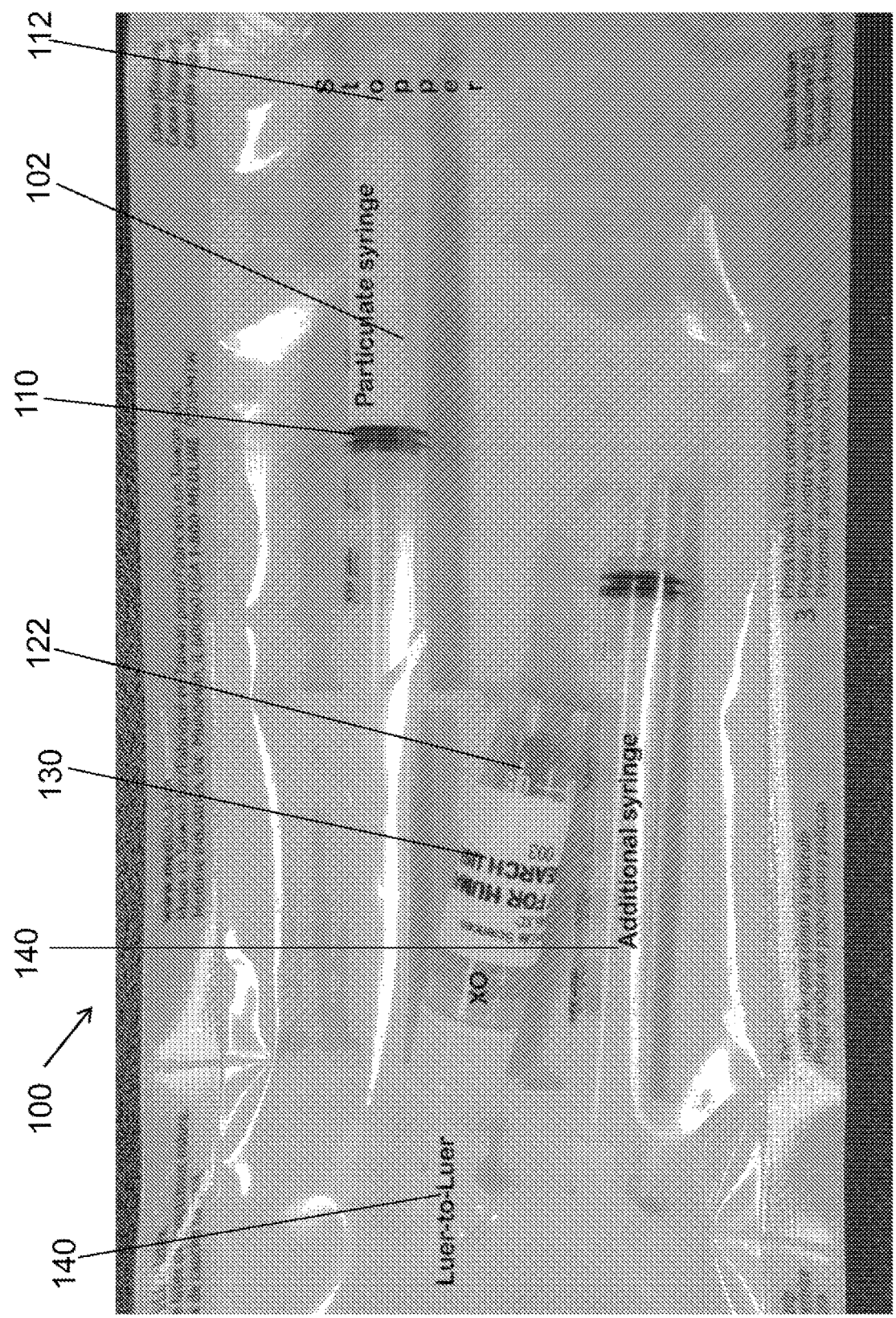
FIG. 2 is a kit including the two parts (i.e., aqueous human umbilical cord filtrate and the micronized human umbilical cord composition) of the two-part clotting composition before mixing each component and reconstituting the particulate part.

After concluding steps (e) and (f), step (g) is performed by placing and sealing the micronized human umbilical cord composition (of step (e)) in a first sterile container for subsequent use and placing and sealing the aqueous human umbilical cord filtrate (of step (f)) in a second sterile container for subsequent use, wherein both the micronized human umbilical cord composition and the aqueous human umbilical cord filtrate are sterile and are configured to form a paste or lotion when admixed with one another. In this aspect, the micronized human umbilical cord composition may be preloaded into a sterile syringe as shown in FIG. 2; and as further shown in FIG. 2, the aqueous human umbilical cord filtrate may be preloaded into a sterile container that is separate from the micronized human umbilical cord composition, with each being sterilized and configured for sterilely mixing the two components together as desired to form the two-part clotting composition configured for wound packing and/or dental purposes and/or dental treatments disclosed herein Kits Containing Two-Part Clotting Composition FIG. 2 depicts a kit (100) comprising the two-part clotting composition configured for wound packing. The two-part clotting composition includes a micronized human umbilical cord composition (102) (obtained by the above described method(s)/process(es)) preloaded into a sterile syringe (110), and an aqueous human umbilical cord filtrate (122) (obtained by the above described method(s)/process(es)) preloaded into a sterile container (130) that is separate from the micronized human umbilical cord composition. As further shown in FIG. 2, the kit may further include an additional (second) syringe (140) as well as a luer-to-luer connector (150) that are both configured for "point of use" preparation and use of the compositions disclosed herein.

Figure 3:
FIG. 3 is a photograph of the two-part clotting composition after the aqueous human umbilical cord filtrate part has been mixed with and reconstituted the micronized human umbilical cord composition.
Figure 4:
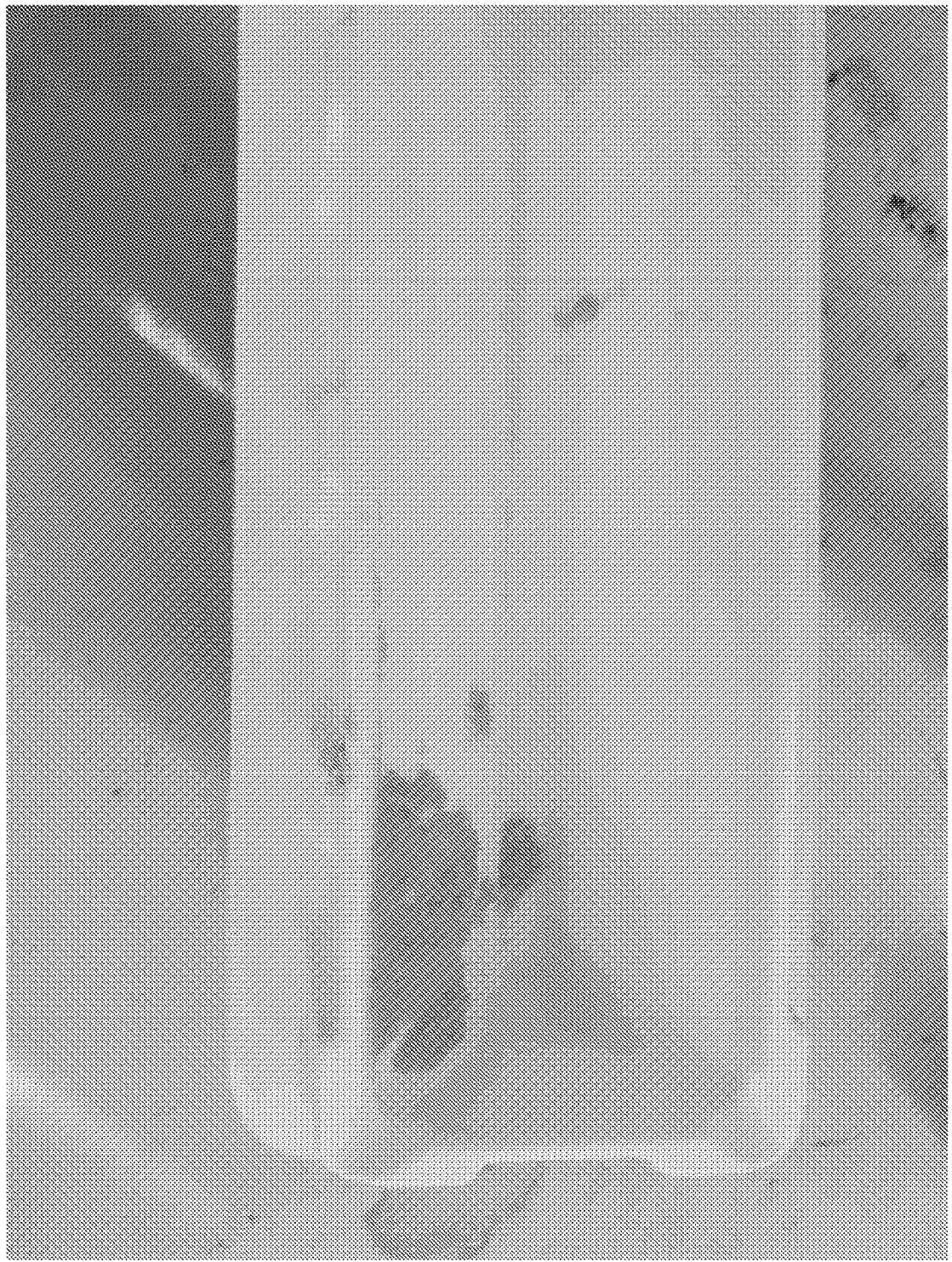
FIG. 4 is another photograph of the two-part clotting composition after the aqueous human umbilical cord filtrate part has been mixed with and reconstituted the micronized human umbilical cord composition.

In view of FIG. 2 and when one desires to reconstitute the micronized human umbilical cord composition with the aqueous human umbilical cord filtrate for point of use applications/purposes during a desired dental and/or medical procedure, the user draws up at least 500 ul of aqueous human umbilical cord filtrate (122) from container (130) into the additional syringe (140). Next, the luer-to-luer connector (150) is attached to the end of this syringe (140). Next, the user holds upright the syringe (110) having the micronized human umbilical cord composition therein and removes the stopper (112). The syringe (140) with filtrate is then connected to the syringe (110) with particulate (102) by the luer-to-luer connector positioned between and directly connected to each syringe. The user then holds the connected syringes (110, 140) in a horizontal orientation and depresses the filtrate containing syringe to move the filtrate into the micronized human umbilical cord composition syringe (110), which is subsequently shaken to facilitate wetting of the micronized human umbilical cord composition by the aqueous human umbilical cord filtrate. The micronized human umbilical cord composition and aqueous human umbilical cord filtrate are further mixed by advancing and retracting the syringe plungers back and forth until sufficient mixing occurs, thereby forming the reconstituted two-part clotting composition. Next, the syringe is removed from the luer-to-luer connector the product is ready to use (point of use) as shown, for example, in FIGS. 3 and 4. During the above mixing steps and post-mixing, it is imperative to maintain proper sterile technique to ensure sterility of the reconstituted two-part clotting composition for its desired end use (e.g., wound packing and/or dental procedure).

Methods of Use

Without wishing to be bound by theory, it is envisioned that the two-part clotting compositions disclosed herein may be particularly useful for wound packing, clotting, and wound healing purposes and would advantageously produce very little immunogenic response to the composition's non-immunogenic characteristics/properties.

Collagen, fibronectin and, hyaluronan found within the composition provide substrate for clotting factors to bind and signaling for cell attachment and growth. VEGFR1, HGF, interleukin antagonists (IL-1ra), bFGF and PDGF-BB provide cell growth signaling and anti-inflammatory effects thereby providing various therapeutic effects such as wound healing.

The advantageous uses may be achieved due to the ease of use (e.g., ease of preparation and ease of readily modifying the composition's viscosity when mixing the micronized human umbilical cord composition and aqueous human umbilical cord filtrate) of the compositions for the desired purpose.

For example, it is envisioned that the compositions disclosed herein may be used for dental purposes (periodontic and/or endodontic purposes) and more particularly for packing a subject's gums post-tooth extraction. In this particular use, a subject's gum(s) are packed with the compositions disclosed herein almost immediately post-tooth extraction. In this aspect, the micronized human umbilical cord composition and aqueous human umbilical cord filtrate are mixed (sterilely mixed) at an effective viscosity to induce blood clotting; and the cavity within the subject's gums formed by the tooth extraction is packed with the mixed composition (sterile composition) to induce blood clotting within the packed cavity. In certain aspects, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate during this method. If very viscous mixed composition is desired, a higher proportion of the micronized human umbilical cord composition is mixed with a lower proportion the aqueous human umbilical cord filtrate, and conversely, if a less viscous mixed composition is desired, a higher proportion of the aqueous human umbilical cord filtrate is mixed with a lower proportion of the micronized human umbilical cord composition. The above-mentioned packing may be repeated as necessary.

While the above specifically envisions dental uses, it is further envisioned that the disclosed compositions may have more general applications in the medical field such as general wound packing (occurring in surgical procedures and/or acute trauma resulting in open external and/or internal wounds) and/or wound healing. In this aspect, it is envisioned that one would initially assess the wound to generally determine the overall viscosity and thickness of the (mixed) two-part composition needed to, for example, pack and/or treat a subject's wound. Next, one sterilely mixes the composition at an effective viscosity to induce blood clotting; and then sterilely packs the subject's wound with the sterilely mixed composition to induce blood clotting within the sterilely packed wound. In certain aspects, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate during this method. If very viscous mixed composition is desired, a higher proportion of the micronized human umbilical cord composition is mixed with a lower proportion the aqueous human umbilical cord filtrate, and conversely, if a less viscous mixed composition is desired, a higher proportion of the aqueous human umbilical cord filtrate is mixed with a lower proportion of the micronized human umbilical cord composition. The above-mentioned packing may be repeated as necessary.

In certain aspects, also disclosed are methods of treating an orthopedic and/or podiatric conditions/ailments. For example, in certain aspects, plantar fasciitis and/or heel ailments may be treated by injecting the mixed two part composition disclosed herein directly into the subject's foot (subcutaneously in a portion between the ball and heel of the foot) and/or immediately adjacent to the portion of bone forming the subject's heel. This method comprises: (a) sterilely mixing the composition disclosed herein at an effective viscosity to treat a subject having orthopedic and/or podiatric conditions/ailments (e.g., plantar fasciitis); and (b) sterilely injecting the sterilely mixed composition of step (a) into and/or adjacent the area of the subject affected with orthopedic and/or podiatric conditions/ailments thereby treating the condition/ailment. In this aspect, the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate to have sufficient viscosity to treat the condition/ailment. For example, when treating ones plantar fasciitis with the above method and compositions, the mixed compositions have sufficient thickness and viscosity to provide cushioning (subcutaneous cushioning) to treat and mitigate pain associated with plantar fasciitis. In particular, the high viscosity of the filtrate provides the desired cushioning effect, and the Wharton's Jelly (mucopolysaccharides and proteoglycans) in the filtrate further aid in the cushioning and protective purposes of the above-mentioned treatment(s).

In certain aspects, each individual component of the two-part clotting compositions disclosed herein may be used individually (alone) for specified purposes. For example, when using the disclosed filtrate individually, the purpose of using all filtrate (only filtrate) would be to provide the growth factors and exosomes within the filtrate without introducing a scaffolding or stromal substrate. For example, if one were to use the filtrate to provide cushioning substance to a degenerative heel pad or mix with commercially available bone particulate for application to a tooth socket. As another example and when using the disclosed micronized compositions individually (alone), the purpose of using all particulate would be to pack a wet wound bed or dental socket when the area is too wet to add additional filtrate, or another filtrate is desired, such as platelet rich plasma (PRP).

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A kit comprising a two-part clotting composition configured for wound packing, the two-part clotting composition comprising:
   (a) a micronized human umbilical cord composition preloaded into a sterile syringe; and
   (b) an aqueous human umbilical cord filtrate preloaded into a sterile container that is separate from the micronized human umbilical cord composition, the aqueous human umbilical cord filtrate is configured to reconstitute the micronized human umbilical cord composition.

2. The kit of claim 1, further comprising a second sterile syringe configured for drawing up the aqueous human umbilical cord filtrate and for subsequent connection to the preloaded sterile syringe having the micronized human umbilical cord composition by a luer-to-luer connector positioned there between.

3. The kit of claim 2, wherein the micronized human umbilical cord is a dried or milled micronized human umbilical cord tissue.

4. The kit of claim 3, wherein the micronized human umbilical cord is a dried or milled micronized human umbilical cord tissue that is not subjected to exogenous enzymatic digestion.

5. The kit of claim 1, wherein the micronized human umbilical cord is a dried or milled micronized human umbilical cord tissue.

6. The kit of claim 5, wherein the micronized human umbilical cord is a dried or milled micronized human umbilical cord tissue that is not subjected to exogenous enzymatic digestion.

7. The kit of claim 1, wherein the micronized human umbilical cord composition has a particle diameter size ranging from greater than 1 µm to less than 300 µm.

8. The kit of claim 7, wherein the micronized human umbilical cord composition is dried micronized human umbilical cord tissue having a particle diameter size ranging from greater than 1 µm to less than 300 µm and comprising collagen, fibronectin, insulin growth factor binding protein-1 (IGFBP-1) at a concentration ranging from 1500 pg/mL to ~9000 pg/mL, sulfated glycosaminogylcans (sGAGs) at a concentration ranging from $0.1 \times 10^6$ pg/ml to $3.0 \times 10^7$ pg/ml, exosomes at a concentration ranging from $1.5 \times 10^9$ particles/ml to $4.0 \times 10^9$ particles/ml and having a particle size ranging from 50 nm to 200 nm, or any combination thereof.

9. The kit of claim 8, wherein the aqueous human umbilical cord filtrate comprises acellular Wharton's jelly, exosomes, endogenous growth factors, hyaluronan (HA) at a concentration ranging from $3.0 \times 10^8$ pg/ml to $4.0 \times 10^8$ pg/ml, vascular endothelial growth factor receptor (VEGFR1) at a concentration ranging from $1.5 \times 10^3$ pg/ml to $2.5 \times 10^3$ pg/ml, hepatocyte growth factor (HGF) at a concentration ranging from $2.0 \times 10^3$ pg/ml to $3.5 \times 10^3$ pg/ml, interleukin antagonists, basic fibroblast growth factor (bFGF) at a concentration ranging from $3.0 \times 10^2$ pg/ml to $4.5 \times 10^2$ pg/ml, platelet derived growth factor-BB (PDGF-BB) at a concentration ranging from $1.0 \times 10^2$ pg/ml to $1.6 \times 10^2$ pg/ml, or a combination thereof.

10. The kit of claim 9, wherein the aqueous human umbilical cord filtrate further comprises an isotonic solution.

11. The kit of claim 10, wherein the isotonic solution is phosphate buffered saline.

12. The kit of claim 11, wherein the aqueous human umbilical cord filtrate comprises particles from a human umbilical cord tissue that are less than 100 µm in diameter therein.

13. The kit of claim 1, wherein the aqueous human umbilical cord filtrate comprises acellular Wharton's jelly, exosomes, endogenous growth factors, hyaluronan (HA) at a concentration ranging from $3.0 \times 10^8$ pg/ml to $4.0 \times 10^8$ pg/ml, vascular endothelial growth factor receptor (VEGFR1) at a concentration ranging from $1.5 \times 10^3$ pg/ml to $2.5 \times 10^3$ pg/ml, hepatocyte growth factor (HGF) at a concentration ranging from $2.0 \times 10^3$ pg/ml to $3.5 \times 10^3$ pg/ml, interleukin antagonists, basic fibroblast growth factor (bFGF) at a concentration ranging from $3.0 \times 10^2$ pg/ml to $4.5 \times 10^2$ pg/ml, platelet derived growth factor-BB (PDGF-BB) at a concentration ranging from $1.0 \times 10^2$ pg/ml to $1.6 \times 10^2$ pg/ml, or a combination thereof.

14. The kit of claim 1, wherein the aqueous human umbilical cord filtrate further comprises an isotonic solution.

15. The kit of claim 14, wherein the isotonic solution is phosphate buffered saline.

16. The kit of claim 1, wherein the aqueous human umbilical cord filtrate comprises particles from a human umbilical cord tissue that are less than 100 µm in diameter therein.

17. A method of packing a subject's gums post-tooth extraction comprising:
   (a) mixing a and b of the two-part clotting composition of claim 1 at an effective viscosity to induce blood clotting; and
   (b) packing a cavity within the subject's gums formed by tooth extraction with the mixed composition of step (a) to induce blood clotting within the packed cavity.

18. The method of claim 17, wherein the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate.

19. A method of packing a subject's wound comprising:
   (a) sterilely mixing (a) and N of the two-part clotting composition of claim 1 at an effective viscosity to induce blood clotting; and
   (b) sterilely packing the subject's wound with the sterilely mixed composition of step (a) to induce blood clotting within the sterilely packed wound.

20. The method of claim 19, wherein the micronized human umbilical cord composition and the aqueous human umbilical cord filtrate are both sterile and non-immunogenic and are mixed at a ratio of 2:1 to 1:2 micronized human umbilical cord composition and the aqueous human umbilical cord filtrate.

21. A method of making a two-part clotting composition configured for wound packing and/or dental purposes and/or dental treatments, the method comprising:
   (a) providing a human umbilical cord;
   (b) washing the human umbilical cord with an isotonic solution;
   (c) grinding the washed human umbilical cord of step (b) thereby forming ground human umbilical cord tissue;
   (d) separating the ground human umbilical cord tissue of step (c) into a solid retentate and an aqueous human umbilical cord supernatant;
   (e) further processing the solid retentate of step (d) into a micronized human umbilical cord composition; and
   (f) filtering the aqueous human umbilical cord supernatant thereby forming an aqueous human umbilical cord filtrate configured to reconstitute the micronized human umbilical cord composition when admixed with one another, the aqueous human umbilical cord filtrate having particles from the ground human umbilical cord tissue that are less than 100 µm in diameter therein, wherein:

none of steps (a)-(f) include introduction of exogenous enzymes resulting in exogenous enzymatic degradation/digestion.

22. The method of claim 21, wherein the human umbilical cord is obtained from a subject and is subsequently subjected to steps (a)-(c) within 48 to 72 hours post-childbirth and/or caesarean section.

23. The method of claim 22, further comprising, between steps (a)-(c), removing any blood clots present within the human umbilical cord.

24. The method of claim 21, further comprising, between steps (a)-(c), removing any blood clots present within the human umbilical cord.

* * * * *